US008742024B2

(12) United States Patent
Bruhns et al.

(10) Patent No.: US 8,742,024 B2
(45) Date of Patent: Jun. 3, 2014

(54) MIXTURE OF SURFACE POSTCROSSLINKED SUPERABSORBERS WITH DIFFERENT SURFACE POSTCROSSLINKING

(75) Inventors: Stefan Bruhns, Mannheim (DE); Thomas Daniel, Waldsee (DE); Dieter Hermeling, Böhl-Iggelheim (DE); Ulrich Riegel, Landstuhl (DE)

(73) Assignee: BASF SE, Ludwigshafen (DE)

( * ) Notice: Subject to any disclaimer, the term of this patent is extended or adjusted under 35 U.S.C. 154(b) by 133 days.

(21) Appl. No.: 13/128,558

(22) PCT Filed: Nov. 12, 2009

(86) PCT No.: PCT/EP2009/065036
§ 371 (c)(1),
(2), (4) Date: May 10, 2011

(87) PCT Pub. No.: WO2010/057823
PCT Pub. Date: May 27, 2010

(65) Prior Publication Data
US 2011/0224379 A1    Sep. 15, 2011

(30) Foreign Application Priority Data
Nov. 21, 2008 (EP) .................................... 08169670

(51) Int. Cl.
*C08F 8/32* (2006.01)
*C08F 8/00* (2006.01)
*C08G 61/08* (2006.01)
*C09D 175/06* (2006.01)
*C08F 8/42* (2006.01)

(52) U.S. Cl.
USPC .................. 525/327.2; 525/327.3; 525/327.4; 525/326.1; 525/520; 525/526; 525/337; 525/55

(58) Field of Classification Search
CPC ............. C09D 133/068; C09D 163/00; C09D 133/062; C09D 133/06; C09D 133/04; C09D 143/04; C08F 8/00; C08F 251/00; C08F 299/00; C08G 59/3209; C08G 59/42; C08G 59/32; C08G 59/20; C08G 59/186; C08G 59/18
USPC ........ 524/486; 525/54.2, 327.2–327.4, 326.1, 525/520, 337, 526, 55
See application file for complete search history.

(56) References Cited

U.S. PATENT DOCUMENTS

| 5,102,597 A * | 4/1992 | Roe et al. ....................... 264/126 |
| 2002/0128616 A1 * | 9/2002 | Morman et al. .............. 604/364 |
| 2004/0265387 A1 * | 12/2004 | Hermeling et al. ........... 424/486 |
| 2007/0161759 A1 * | 7/2007 | Riegel et al. .................. 525/375 |
| 2008/0125734 A1 | 5/2008 | Muthiah et al. |

FOREIGN PATENT DOCUMENTS

| DE | 102005036992 A1 | 2/2007 |
| EP | 0691133 A1 | 1/1996 |

OTHER PUBLICATIONS

Buchholz, Fredric L., et al,. Modern Superabsorbent Polymer Technology, "Commercial Processes for the Manufacture of Superabsorbent Polymers," pp. 69-117. New York: John Wiley & Sons, Inc., 1998.
International Search Report in PCT Application No. PCT/EP2009/065036, dated Jan. 21, 2010.

* cited by examiner

*Primary Examiner* — Mark Eashoo
*Assistant Examiner* — Marilou Lacap
(74) *Attorney, Agent, or Firm* — Marshall, Gerstein & Borun LLP

(57) ABSTRACT

A mixture of superabsorbents having differing surface postcrosslinking, more particularly a mixture of differingly surface-postcrosslinked sieve cuts of a base polymer, exhibits improved absorption and retention over a unitarily surface-postcrosslinked superabsorbent.

3 Claims, No Drawings under pressure a multiple of their own weight of water. In general, such a superabsorbent will have a Centrifuge Retention Capacity (CRC, method of measurement given hereinbelow) of at least 5 g/g, preferably at least 10 gig and more preferably at least 15 g/g. A superabsorbent can also be a mixture of chemically different individual superabsorbents or of components which do not have superabsorbent properties until they cooperate, so it is less its chemical composition which makes a superabsorbent but the fact that it has superabsorbent (superabsorbing) properties.

MIXTURE OF SURFACE POSTCROSSLINKED SUPERABSORBERS WITH DIFFERENT SURFACE POSTCROSSLINKING

CROSS-REFERENCE TO RELATED APPLICATIONS

This is the U.S. national phase application of International Application No. PCT/EP2009/065036, filed Nov. 12, 2009, which claims the benefit of European patent application No. 08169670.0, filed Nov. 21, 2008.

The present invention relates to a mixture of surface-postcrosslinked superabsorbents having differing surface postcrosslinking. More particularly, the present invention relates to a mixture of superabsorbents of differing average particle size, which are differingly surface-postcrosslinked. The present invention further relates to a process for producing such a mixture and also to its use and to hygiene articles comprising such a mixture.

Superabsorbents are known. Materials of this type are also commonly known by designations such as "high-swellability polymer" "hydrogel" (often even used for the dry form), "hydrogel-forming polymer", "water-absorbing polymer", "absorbent gel-forming material", "swellable resin", "water-absorbing resin", "water-absorbing polymer" or the like. The materials in question are crosslinked hydrophilic polymers, more particularly polymers formed from (co)polymerized hydrophilic monomers, graft (co)polymers of one or more hydrophilic monomers on a suitable grafting base, crosslinked ethers of cellulose or of starch, crosslinked carboxymethylcellulose, partially crosslinked polyalkylene oxide or natural products that are swellable in aqueous fluids, examples being guar derivatives, of which superabsorbents based on partially neutralized acrylic acid are most widely used. The essential properties of superabsorbents are their ability to absorb and retain amounts of aqueous fluids equivalent to many times their own weight, even under moderate pressure. A superabsorbent which is used in the form of a dry powder transforms into a gel on taking up liquid, specifically into a hydrogel when as usual taking up water. Their crosslinking distinguishes synthetic superabsorbents in an essential and important way from customary merely thickeners, since the crosslinking renders the polymers insoluble in water. Soluble substances would have no utility as superabsorbents. By far the most important field of use for superabsorbents is to absorb bodily fluids. Superabsorbents are used for example in diapers for infants, incontinence products for adults or feminine hygiene products. Examples of other fields of use are as water-retaining agents in market gardening, as water storage media for protection against fire, for fluid absorption in food packaging or, very generally, for absorption of moisture.

Superabsorbents are capable of absorbing and retaining under pressure a multiple of their own weight of water. In general, such a superabsorbent will have a Centrifuge Retention Capacity (CRC, method of measurement given hereinbelow) of at least 5 g/g, preferably at least 10 gig and more preferably at least 15 g/g. A superabsorbent can also be a mixture of chemically different individual superabsorbents or of components which do not have superabsorbent properties until they cooperate, so it is less its chemical composition which makes a superabsorbent but the fact that it has superabsorbent (superabsorbing) properties.

Not just its absorption capacity is important for a superabsorbent, but also the ability to retain liquid under pressure (retention, usually expressed as Absorption Under Load (AUL) or Absorption Against Pressure (AAP)) and also to transport liquid in the swollen state (usually expressed as Saline Flow Conductivity (SFC)). Swollen gel can impair or even block (gel blocking) the transportation of liquid to as yet unswollen superabsorbent. Good transportation properties for liquids are possessed for example by hydrogels having high gel strength in the swollen state. Gels lacking in strength are deformable under an applied pressure, for example pressure due to body weight, and clog the pores in the superabsorbent/cellulose fiber absorbent and so prevent continued absorption of fluid. Enhanced gel strength is generally obtained through a higher degree of crosslinking, although this reduces the absorption capacity of the product. An elegant way to enhance gel strength is to increase the degree of crosslinking at the surface of the superabsorbent particle compared with the interior of the particle. Dried superabsorbent particles having an average crosslink density are subjected to additional crosslinking in a thin surface layer of their particles, usually in a surface postcrosslinking step. Surface postcrosslinking increases the crosslink density in the surface shell of the superabsorbent particles, raising their absorbency under load to a higher level. Whereas absorption capacity decreases in the surface layer of the superabsorbent particles, their core has an improved absorption capacity (compared to the shell) owing to the presence of mobile chains of polymer, so that shell construction ensures improved fluid transmission without occurrence of the gel-blocking effect. It is likewise known to produce altogether more highly crosslinked superabsorbents and to subsequently reduce the degree of crosslinking in the interior of the particles compared with an outer shell of the particles.

Processes for producing superabsorbents are also known. Superabsorbents based on acrylic acid, which are the most common form of superabsorbent on the market, are produced by free-radical polymerization of acrylic acid in the presence of a crosslinker (the "internal crosslinker"), with the acrylic acid being partially neutralized, typically by addition of alkali, usually aqueous sodium hydroxide solution, before, after or partly before, partly after the polymerization. The polymer gel thus obtained is comminuted (which, depending on the polymerization reactor used, can take place concurrently with the polymerization) and dried. The dry powder thus obtained (the "base polymer") is typically postcrosslinked at the surface of the particles by reacting it with further crosslinkers such as, for example, organic crosslinkers or multivalent cations, for example aluminum (usually used in the form of aluminum sulfate), or both, to produce a more highly crosslinked surface layer compared with the particle interior.

Fredric L. Buchholz and Andrew T. Graham (editors) provide a comprehensive overview of superabsorbents, their properties and processes for producing superabsorbents in "Modern Superabsorbent Polymer Technology", J. Wiley & Sons, New York, U.S.A./Wiley-VCH, Weinheim, Germany, 1997, ISBN 0-471-19411-5.

EP 691 133 A1 teaches a mixture of superabsorbents having differing absorption capacity and differing absorption capacity under pressure. The mixture comprises mixing different non-surface-postcrosslinked superabsorbents or a non-surface-postcrosslinked superabsorbent with a surface-postcrosslinked superabsorbent.

The objective continues to be that of finding new or improved superabsorbents and processes for producing such superabsorbents. More particularly, increasing the absorption capacity (CRC) and also the retention or the absorbency under load (AUL) of the superabsorbent is a constant objective.

Accordingly, a mixture of superabsorbents having differing surface postcrosslinking was found. The mixture is notable for higher CRC and AUL values compared with a unitarily surface-postcrosslinked superabsorbent. A process for producing such mixtures was also found, uses of these superabsorbent mixtures and also hygiene articles comprising these superabsorbent mixtures.

The superabsorbent mixture of the present invention can be produced by mixing two or more differingly surface-postcrosslinked superabsorbents using any desired method of mixing. Three, four, five or any other desired number of differingly surface-postcrosslinked superabsorbents can also be mixed. Surface-postcrosslinked superabsorbents per se are known as are mixing processes.

Differingly surface-postcrosslinked superabsorbents are superabsorbents which were differingly treated with surface-postcrosslinking agent in terms of type, amount and/or after-treatment and as a result were differingly surface-postcrosslinked. Nonlimiting examples of differingly surface-postcrosslinked superabsorbents are, for instance, superabsorbents endowed with differing amounts of surface-postcrosslinking agent (in % by weight of surface-postcrosslinking agent, based on the particular base polymer), superabsorbents endowed with differing surface-postcrosslinking agents, or superabsorbents which, following application of the surface-postcrosslinking agent, were after-treated differingly, more particularly at differing temperature or for differing duration. Superabsorbents differing only in one such feature, in two or more or in all can be mixed.

The differingly surface-postcrosslinked superabsorbents can, but need not, differ in the degree of surface postcrosslinking. The degree of surface postcrosslinking can be determined indirectly via the decrease in the CRC of the superabsorbent, since CRC decreases with the degree of surface postcrosslinking. The increase in the SFC can also be used as a measure of the degree of surface postcrosslinking, particularly when further additives influence the permeability of the swollen superabsorbent.

Mixing can take place after surface postcrosslinking, but also during surface postcrosslinking. When mixing takes place during surface postcrosslinking the constituents of the mixture will pass through part of the surface postcrosslinking conjointly. Particularly in the case of the commonly used processes for surface postcrosslinking, which comprise a step for endowing the base polymer with surface-postcrosslinking agent and a subsequent heat-treatment step to complete the surface postcrosslinking, the heat treatment is typically carried out in a heated apparatus which effects continuous conveyance by commixing. Apparatuses of this type are frequently used in the chemical industry to dry powders and they are usually simply referred to as continuous "dryers". Feeding base polymers separately endowed with surface-postcrosslinking agent into such a dryer at different points leads to a mixture of superabsorbents differingly surface-postcrosslinked as a result of differing heat-treatment duration at least, and is a particularly convenient method of producing a mixture which is in accordance with the present invention. This method of making can additionally utilize different base polymers, different surface-postcrosslinking agents and/or different amounts of one or more surface-postcrosslinking agents, and also dryers having different temperature zones in order that differing surface postcrosslinking may be created not just through differing residence time but also through differing temperature.

In one preferred embodiment of the present invention, the mixture of superabsorbents having differing surface postcrosslinking comprises a mixture of differingly surface-postcrosslinked sieve cuts of a base polymer.

The mixture of the present invention can be essentially a mixture of differingly surface-postcrosslinked sieve cuts of a base polymer or else a mixture of differingly surface-postcrosslinked sieve cuts of a base polymer, i.e., consist of differingly surface-postcrosslinked sieve cuts of a base polymer.

"Sieve cut" in the context of this invention is to be understood as meaning a fraction from the entire particle size distribution of a base polymer. Different sieve cuts differ in average particle size, which can be determined either by sieve analysis or by optical methods such as light scattering or laser diffraction. Fractions of this type are usually recovered by sieving. However, they can also be obtained by other methods of classification, for instance by wind sifting including separation in the air stream in cyclones, although minor secondary effects can arise in such processes, due to density or particle shape for example, and are routinely taken into account.

In principle, any desired number of sieve cuts can be present in the mixture. Preferably, the mixture comprises two, three or four sieve cuts, more preferably two or three sieve cuts and most preferably two sieve cuts.

In one preferred embodiment of the present invention, the mixture comprises at least two different sieve cuts of a base polymer which were separately endowed with surface-postcrosslinking agent and then heat-treated for different lengths of time. A particularly simple way of obtaining such a mixture is to feed the surface-postcrosslinking agent endowed sieve cuts at various points of a heated apparatus which effects continuous conveyance by commixing (a continuous dryer), so that the individual sieve cuts are heat-treated for differing duration. More preferably, the mixture of the present invention comprises sieve cuts heat-treated the longer the smaller their average particle size diameter is.

The superabsorbents present in the mixture of the present invention are obtainable in different ways, for example by solution polymerization, suspension polymerization, dropletization or spray polymerization. Processes of this type are known.

A preferred present-invention polymerization process for producing acrylate superabsorbents is the aqueous solution polymerization of a monomer mixture comprising a) at least one ethylenically unsaturated acid-functional monomer which optionally is at least partly present as a salt,
b) at least one crosslinker,
c) at least one initiator,
d) optionally one or more ethylenically unsaturated monomers copolymerizable with the monomers mentioned under a), and
e) optionally one or more water-soluble polymers.

The monomers a) are preferably water-soluble, i.e., their solubility in water at 23° C. is typically at least 1 g/100 g of water, preferably at least 5 g/100 g of water, more preferably at least 25 g/100 g of water and most preferably at least 35 g/100 g of water.

Suitable monomers a) are for example ethylenically unsaturated carboxylic acids or their salts, such as acrylic acid, methacrylic acid, maleic acid, maleic anhydride, and itaconic acid or its salts. Particularly preferred monomers are acrylic acid and methacrylic acid. Acrylic acid is very particularly preferred.

Further suitable monomers a) are for example ethylenically unsaturated sulfonic acids, such as styrenesulfonic acid and 2-acrylamido-2-methylpropanesulfonic acid (AMPS).

Impurities can have an appreciable influence on the polymerization. Therefore, the raw materials used should be very pure. It is accordingly often advantageous to specially purify the monomers a). Suitable methods of purification are described for example in WO 2002/055469 A1, WO 2003/078378 A1 and WO 2004/035514 A1. A suitable monomer a) is for example an acrylic acid purified as described in WO 2004/035514 A1 to comprise 99.8460% by weiaht of acrylic acid, 0.0950% by weight of acetic acid, 0.0332% by weight of water, 0.0203% by weight of propionic acid, 0.0001% by weight of furfurals, 0.0001% by weight of maleic anhydride, 0.0003% by weight of diacrylic acid and 0.0050% by weight of hydroquinone monomethyl ether.

The proportion of the total amount of monomers a) which is attributable to acrylic acid and/or salts thereof is preferably at least 50 mol %, more preferably at least 90 mol % and most preferably at least 95 mol %.

The monomer solution comprises preferably at most 250 weiaht ppm, more preferably at most 130 weight ppm and even more preferably 70 weight ppm and also preferably at least 10 weight ppm, more preferably at least 30 weight ppm and especially around 50 weight ppm of hydroquinone monoether, all based on the nonneutralized monomer a), with neutralized monomer a), i.e., a salt of monomer a), being arithmetically counted as nonneutralized monomer. For example, the monomer solution is obtainable using an ethylenically unsaturated acid-functional monomer having an appropriate hydroquinone monoether content.

Preferred hydroquinone monoethers are hydroquinone monomethyl ether (MEHQ) and/or alpha-tocopherol (vitamin E).

Suitable crosslinkers b) ("internal crosslinkers") are compounds having at least two groups suitable for crosslinking. Groups of this type are for example ethylenically unsaturated groups which can be free-radically interpolymerized into the polymer chain; and functional groups capable of forming covalent bonds with the acid groups of monomer a). Suitable crosslinkers b) further include polyvalent metal salts capable of forming coordinative bonds with at least two acid groups of monomer a).

Crosslinkers b) are preferably compounds having at least two polymerizable groups which can be free-radically interpolymerized into the polymer network. Suitable crosslinkers b) are for example ethylene glycol dimethacrylate, diethylene glycol diacrylate, polyethylene glycol diacrylate, allyl methacrylate, trimethylolpropane triacrylate, triallylamine, tetraallylammonium chloride, tetraallyloxyethane as described in EP 530 438 A1, di- and triacrylates as described in EP 547 847 A1, EP 559 476 A1, EP 632 068 A1, WO 93/21237 A1. WO 2003/104299 A1, WO 2003/104300 A1. WO 2003/104301 A1 and DE 103 31 450 A1, mixed acrylates which, as well as acrylate groups, comprise further ethylenically unsaturated groups, as described in DE 103 31 456 A1 and DE 103 55 401 A1, or crosslinker mixtures as described for example in DE 195 43 368 A1, DE 196 46 484 A1, WO 90/15830 A1 and WO 2002/32962 A2.

Preferred crosslinkers b) are pentaerythritol triallyl ether, tetraallyloxyethane, methylenebismethacrylamide, 10- to 20-tuply ethoxylated trimethylolpropane triacrylate, 10- to 20-tuply ethoxylated trimethylolethane triacrylate, more preferably 15-tuply ethoxylated trimethylolpropane triacrylate, polyethylene glycol diacrylates having 4 to 30 ethylene oxide units in the polyethylene glycol chain, trimethylolpropane triacrylate, di- and triacrylates of 3- to 30-tuply ethoxylated glycerol, more preferably di- and triacrylates of 10- to 20-tuply ethoxylated glycerol, and triallylamine. Polyols not fully esterified with acrylic acid can also be present here as Michael adducts with themselves, in which case tetra-, penta- or even higher acrylates can also be present.

Very particularly preferred crosslinkers b) are the diacrylated, dimethacrylated, triacrylated or trimethacrylated multiply ethoxylated and/or propoxylated glycerols as described in WO 2003/104301 A1 for example. Di- and/or triacrylates of 3- to 10-tuply ethoxylated glycerol are particularly advantageous. Very particular preference is given to di- or triacrylates of 1- to 5-tuply ethoxylated and/or propoxylated glycerol. The triacrylates of 3- to 5-tuply ethoxylated and/or propoxylated glycerol are most preferable, especially the triacrylate of 3-tuply ethoxylated glycerol.

The amount of crosslinker b) is preferably in the range from 0.05% to 1.5% by weight, more preferably in the range from 0.1% to 1% by weight and most preferably in the range from 0.3% to 0.6% by weight, all based on monomer a). As crosslinker content increases, Centrifuge Retention Capacity (CRC) decreases and absorbency under a pressure of 0.3 psi (AUL 0.3 psi) increases.

Useful initiators c) include any compounds that produce free radicals under the polymerization conditions, examples being thermal initiators, redox initiators, photoinitiators. Suitable redox initiators are sodium peroxodisulfate/ascorbic acid, hydrogen peroxide/ascorbic acid, sodium peroxodisulfate/sodium bisulfite and hydrogen peroxide/sodium bisulfite. Preference is given to using mixtures of thermal initiators and redox initiators, such as sodium peroxodisulfate/hydrogen peroxide/ascorbic acid. But the reducing component is preferably a mixture of the sodium salt of 2-hydroxy-2-sulfinatoacetic acid, the disodium salt of 2-hydroxy-2-sulfonatoacetic acid and sodium bisulfite (available as Brüggolit® FF6M or Brüggolit® FF7, alternatively BRUGGOLITE® FF6M or BRUGGOLITE® FF7 from L. Brüggemann K G, Salzstraße 131, 74076 Heilbronn, Germany, www.brueggemann.com).

Ethylenically unsaturated monomers d) copolymerizable with the ethylenically unsaturated acid-functional monomers a) are for example acrylamide, methacrylamide, hydroxyethyl acrylate, hydroxyethyl methacrylate, dimethylaminoethyl methacrylate, dimethylaminoethyl acrylate, dimethylaminopropyl acrylate, diethylaminopropyl acrylate, dimethylaminoethyl methacrylate, diethylaminoethyl methacrylate, maleic acid and maleic anhydride.

Useful water-soluble polymers e) include polyvinyl alcohol, polyvinylpyrrolidone, starch, starch derivatives, modified cellulose, such as methylcellulose or hydroxyethylcellulose, gelatin, polyglycols or polyacrylic acids, preferably starch, starch derivatives and modified cellulose.

An aqueous monomer solution is typically used. The water content of the monomer solution is preferably in the range from 40% to 75% by weight, more preferably in the range from 45% to 70% by weight and most preferably in the range from 50% to 65% by weight. It is also possible to use monomer suspensions, i.e., supersaturated solutions of monomer. Increasing water content means increasing energy requirements at the subsequent drying and a decreasing water content may mean inadequate removal of the heat of polymerization.

The preferred polymerization inhibitors require dissolved oxygen for optimum effect. Therefore, the monomer solution can be freed of dissolved oxygen prior to the polymerization, by inertizing the monomer solution, i.e., by flowing an inert gas, preferably nitrogen or carbon dioxide, through it. The oxygen content of the monomer solution is preferably lowered to less than 1 weight ppm, more preferably to less than 0.5 weight ppm and most preferably to less than 0.1 weight ppm prior to the polymerization.

The monomer mixture may comprise further components. Examples of further components used in monomer mixtures of this type are, for instance, chelating agents in order that metal ions may be kept in solution.

Suitable polymerization reactors are for example kneading reactors or belt reactors. A kneader utilizes for example contrarotatory stirring shafts to continuously comminute the polymer gel formed in the polymerization of an aqueous monomer solution or suspension, as described in WO 2001/38402 A1. Polymerization on a belt is described in DE 38 25 366 A1 and U.S. Pat. No. 6,241,928 for example. Polymerization in a belt reactor produces a polymer gel that has to be comminuted in a further process step, for example in a mincer, extruder, or kneader. However, it is also possible to produce spherical particles of superabsorbent via suspension, sprayed or dropletized polymerization processes.

The acid groups of the polymer gels obtained are typically in a partly neutralized state. Neutralization is preferably performed at the monomer stage; that is, salts of the acid-functional monomers or, to be precise, a mixture of acid-functional monomers and salts of acid-functional monomers ("partially neutralized acid") are used in the polymerization as component a). This is typically accomplished by incorporating the neutralizing agent as an aqueous solution, or else preferably as a solid, into the monomer mixture intended for the polymerization, or preferably into the acid-functional monomer or a solution thereof. The degree of neutralization is preferably in the range from 25 to 95 mol %, more preferably in the range from 50 to 80 mol % and most preferably in the range from 65 to 72 mol %, and the customary neutralizing agents can be used, preferably alkali metal hydroxides, alkali metal oxides, alkali metal carbonates or alkali metal bicarbonates and also mixtures thereof. Instead of alkali metal salts, ammonium salts can also be used. Sodium and potassium are particularly preferred for use as alkali metal cations, but sodium hydroxide, sodium carbonate or sodium bicarbonate and also mixtures thereof are very particularly preferred.

Neutralization can also be carried out after polymerization, at the stage of the polymer gel formed in the polymerization. It is further possible to neutralize up to 40 mol %, preferably from 10 to 30 mol % and more preferably from 15 to 25 mol % of the acid groups prior to polymerization by adding some of the neutralizing agent to the monomer solution and setting the desired final degree of neutralization only after the polymerization, at the polymer gel stage. When the polymer gel is at least partially neutralized after polymerization, the polymer gel is preferably subjected to mechanical comminution, using an extruder for example, in which case the neutralizing agent can be sprayed, sprinkled or poured on and then carefully mixed in. To this end, the gel mass obtained can further be repeatedly extruded for homogenization.

It is preferable, however, to neutralize at the monomer stage. In other words it is a very particularly preferred embodiment to use as monomer a) a mixture of 25 to 95 mol %, more preferably from 50 to 80 mol % and most preferably from 65 to 72 mol % of salt of the acid-functional monomer and a balancing amount (to 100 mol %) of acid-functional monomer. This mixture is for example a mixture of sodium acrylate and acrylic acid, or a mixture of potassium acrylate and acrylic acid.

A preferred embodiment comprises neutralizing using a neutralizing agent having an iron content of generally below 10 weight ppm, preferably below 2 weight ppm and more preferably below 1 weight ppm. It is similarly desirable to have a low level of chloride and also of anions of oxygen acids of chlorine. A suitable neutralizing agent is for example the 50% by weight aqueous sodium hydroxide or potassium hydroxide solution traded as membrane grade, although the amalgam grade or mercury process grade 50% by weight aqueous sodium hydroxide or potassium hydroxide solution is purer and preferable, albeit also costlier.

The polymer gel obtained from the aqueous solution polymerization with or without subsequent neutralization is then preferably dried using a belt dryer until the residual moisture content is preferably in the range from 0.5% to 15% by weight, more preferably in the range from 1% to 10% by weight and most preferably in the range from 2% to 8% by weight (see hereinbelow for method of measuring the residual moisture or water content). When the residual moisture content is too high, the dried polymer gel will have an excessively low glass transition temperature Tg and is difficult to further process. When the residual moisture content is too low, the dried polym is too brittle and the subsequent comminuting steps generate undesirably large amounts of polymer particles of excessively low particle size "fines". The solids content of the gel before drying is generally in the range from 25% to 90% by weight, preferably in the range from 30% to 80% by weight, more preferably in the range from 35% to 70% by weight and most preferably in the range from 40% to 60% by weight. Alternatively, a fluidized bed dryer or a heatable mixer having a mechanical mixing member such as, for example, a paddle dryer or a similar dryer having differently designed mixing implements can be used. Optionally, the dryer can be operated under nitrogen or some other nonoxidizing inert gas or at least under reduced partial pressure of the oxygen in order that oxidative yellowing processes may be prevented. Generally, however, sufficient venting and removal of water vapor also leads to an acceptable product. A very short drying time is generally advantageous with regard to color and product quality. To this end, the commonly used belt dryers are typically operated with the temperature of the drying gas used being at least 50° C., preferably at least 80° C. and more preferably at least 100° C. and also generally at most 250° C., preferably at most 200° C. and more preferably at most 180° C. Commonly used belt dryers often have a plurality of chambers, and the temperature in these chambers can differ. For every type of dryer operating conditions must overall be chosen in a conventional manner such that the desired outcome is achieved for the drying operation.

Drying also reduces the residual monomer content of the polymer particles and destroys final traces of the initiator.

The dried polymer gel is subsequently ground and classified, useful grinding apparatus typically including roll stands having one or more stages, preferably two or three stages, pin mills, hammer mills or swing mills. Oversize clumps of gel which are often still undried in the interior are rubbery, lead to problems at grinding and preferably are removed before grinding, which can simply be done by wind sifting or by means of a sieve (acting as a protective screen for the mill). The mesh size of this protective screen sieve must be chosen on the basis of the mill used, such that there are ideally no disruptions due to excessively large, rubbery particles.

Particles of superabsorbent that are too lame because of insufficiently fine grinding are noticeable as coarse particles in hygiene products such as diapers, their predominant use, they also lower the average rate of swelling of the superabsorbent. Neither is desirable. It is accordingly advantageous to remove coarsely granular polymer particles from the product. This is done using customary methods of classification, for example wind sifting or by sieving through a sieve having a mesh size of at most 1000 μm, preferably at most 900 μm, more preferably at most 850 μm and most preferably at most 800 μm. Sieves of 700 μm, 650 μm or 600 μm mesh size are used for example. The coarsely granular polymer particles ("oversize") removed can be recycled to the grinding and sieving circuit, or further processed separately, for cost optimization.

Polymer particles that are too small in terms of particle size decrease permeability (SFC). It is accordingly advantageous to also remove finely granular polymer particles in the course of this classification. A convenient way to do this, if sieving is chosen, is by using a sieve having a mesh size of at most 300 μm, preferably at most 200 μm, more preferably at most 150 μm and most preferably at most 100 μm. The removed finely granular polymer particles ("undersize" or "fines") can be returned to the monomer stream, the polymerizing gel or the polymerized gel, prior to drying of the gel, in any desired manner by way of cost optimization.

The average particle size of the polymer particles removed as a product fraction is generally at least 200 μm, preferably at least 250 μm and preferably at least 300 μm and also generally at most 600 μm and preferably at most 500 μm. The proportion of particles having a particle size of at least 150 μm is generally at least 90% by weight, preferably at least 95% by weight and more preferably at least 98% by weight. The proportion of particles having a particle size of at most 850 μm is generally at least 90% by weight, preferably at least 95% by weight and more preferably at least 98% by weight.

The polymer thus obtained has superabsorbent properties and hence comes within the term "superabsorbent". Its CRC is typically comparatively high, while its AUL or SFC is comparatively low. Such a non-surface-postcrosslinked superabsorbent is often referred to as "foundational polymer" or "base polymer", to distinguish it from a surface-postcrosslinked superabsorbent produced therefrom.

The superabsorbent particles are surface postcrosslinked to further improve their properties, more particularly increase their AUL and SFC values (reducing the CRC value). Mixing at least two differingly postcrosslinked superabsorbents leads to the superabsorbent mixture of the present invention. The foundational polymers used for surface postcrosslinking can be identical or different.

In a preferred embodiment of the present invention, the product fraction of the foundational polymer (i.e., the fraction which is neither undersize nor oversize) is divided into at least two sieve cuts or recovered in at least two sieve cuts, which are subsequently surface-postcrosslinked differingly and mixed together to form the mixture of the present invention. To this end, the foundational polymer recovered in a first sieving step can be once more separated in a second step into two or more sieve cuts, or concurrently with the removal of over- and/or undersize, the product fraction can be recovered in a plurality of sieve cuts. As mentioned, classification need not necessarily be by sieving, but may take the form of any known method of classification. Sieving is merely the method which is the most convenient in most cases.

One nonlimiting example of a possible separation into sieve cuts is, for instance, the recovery of a fraction of 100-850 μm particle size diameter as a product fraction (i.e., particles that do not pass through a sieve of 850 μm mesh size are separated off as oversize and particles that are not retained on a sieve of 150 μm mesh size are separated off as undersize) which is recovered in two sieve fractions of 100-400 and 400-850 μm particle size diameter through use of an inter-sieve 400 μm in mesh size. Similarly, other product fractions and other sieve cuts are recoverable through use of multiple and/or other inter-sieves.

Suitable postcrosslinkers are compounds comprising groups capable of forming bonds with at least two functional groups of the superabsorbent particles. Suitable surface post-crosslinkers in the case of the market-dominating superabsorbents based on acrylic acid/sodium acrylate are compounds comprising groups capable of forming bonds with at least two carboxylate groups. Preferred postcrosslinkers are amide acetals or carbamates of the general formula (I)

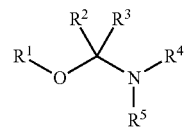

(I)

where $R^1$ is $C_1$-$C_{12}$-alkyl, $C_2$-$C_{12}$-hydroxyalkyl, $C_2$-$C_{12}$-alkenyl or $C_6$-$C_{12}$-aryl, $R^2$ is X or $OR^6$, $R^3$ is hydrogen, $C_1$-$C_{12}$-alkyl, $C_2$-$C_{12}$-hydroxyalkyl, $C_2$-$C_{12}$-alkenyl or $C_6$-$C_{12}$-aryl or X, $R^4$ is $C_1$-$C_{12}$-alkyl, $C_2$-$C_{12}$-hydroxyalkyl, $C_2$-$C_{12}$-alkenyl or $C_6$-$C_{12}$-aryl, $R^5$ is hydrogen, $C_1$-$C_{12}$-alkyl, $C_2$-$C_{12}$-hydroxyalkyl, $C_2$-$C_{12}$-alkenyl, $C_1$-$C_{12}$-acyl or $C_6$-$C_{12}$-aryl.

$R^6$ is $C_1$-$C_{12}$-alkyl, $C_2$-$C_{12}$-hydroxyalkyl, $C_2$-$C_{12}$-alkenyl or $C_6$-$C_{12}$-aryl and X is a carbonyl oxygen common to $R^2$ and $R^3$, wherein $R^1$ and $R^4$ and/or $R^5$ and $R^6$ may be bridged $C_2$-$C_6$-alkanediyl, and wherein the abovementioned radicals $R^1$ to $R^6$ may additionally have altogether one to two free valences, and may be joined via these free valences to at least one suitable foundational structure, or polyhydric alcohols, in which case the polyhydric alcohol preferably has a molecular weight of less than 100 g/mol, more preferably of less than 90 g/mol, even more preferably of less than 80 g/mol and most preferably of less than 70 g/mol, per hydroxyl group and also non vicinal, geminal, secondary or tertiary hydroxyl groups, and polyhydric alcohols are either diols of the general formula (IIa)

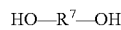

(IIa)

where $R^7$ is either an unbranched dialkyl radical of the formula —$(CH_2)_n$—, where n is an integer from 3 to 20 and preferably from 3 to 12, and both the hydroxyl groups are terminal, or $R^7$ is an unbranched, branched or cyclic dialkyl radical, or polyols of the general formula (IIb)

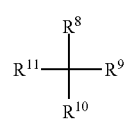

(IIb)

where the radicals $R^8$, $R^9$, $R^{10}$, $R^{11}$ are each independently hydrogen, hydroxyl, hydroxymethyl, hydroxyethyloxymethyl, 1-hydroxyprop-2-yloxymethyl, 2-hydroxypropyloxymethyl, methyl, ethyl, n-propyl, isopropyl, n-butyl, n-pentyl, n-hexyl, 1,2-dihydroxyethyl, 2-hydroxyethyl, 3-hydroxypropyl or 4-hydroxybutyl and altogether 2, 3, or 4, preferably 2 or 3, hydroxyl groups are present, and not more than one of $R^8$, $R^9$, $R^{10}$ and $R^{11}$ is hydroxyl, or cyclic carbonates of the general formula (III)

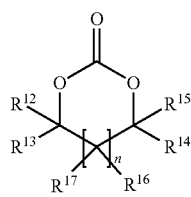

(III)

where $R^{12}$, $R^{13}$, $R^{14}$, $R^{15}$, $R^{16}$ and $R^{17}$ are each independently hydrogen, methyl, ethyl, n-propyl, isopropyl, n-butyl, sec-butyl or isobutyl, and n is either 0 or 1,
or bisoxazolines of the general formula (IV)

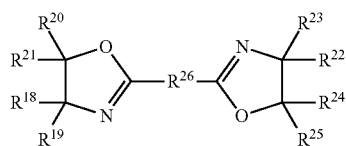

(IV)

where $R^{18}$, $R^{19}$, $R^{20}$, $R^{21}$, $R^{22}$, $R^{23}$, $R^{24}$ and $R^{25}$ are each independently hydrogen, methyl, ethyl, n-propyl, isopropyl, n-butyl, sec-butyl or isobutyl and $R^{26}$ is a single bond, a linear, branched or cyclic $C_2$-$C_{12}$-dialkyl radical, or a polyalkoxydiyl radical constructed of from one to ten ethylene oxide and/or propylene oxide units, as possessed by polyglycol dicarboxylic acids for example.

Preferred postcrosslinkers of the general formula (II) are 2-oxazolidones, such as 2-oxazolidone and N-(2-hydroxyethyl)-2-oxazolidone, N-methyl-2-oxazolidone, N-acyl-2-oxazolidones, such as N-acetyl-2-oxazolidone, 2-oxotetrahydro-1,3-oxazine, bicyclic amide acetals, such as 5-methyl-1-aza-4,6-dioxabicyclo[3.3.0]octane, 1-aza-4,6-dioxa-bicyclo[3.3.0]octane and 5-isopropyl-1-aza-4,6-dioxabicyclo[3.3.0] octane, bis-2-oxazolidones and poly-2-oxazolidones.

Particularly preferred postcrosslinkers of the general formula (I) are 2-oxazolidone, N-methyl-2-oxazolidone. N-(2-hydroxyethyl)-2-oxazolidone and N-hydroxypropyl-2-oxazolidone.

Preferred postcrosslinkers of the general formula (IIa) are 1,3-propanediol, 1,5-pentanediol, 1,6-hexanediol and 1,7-heptanediol. Further examples of postcrosslinkers of formula (IIa) are 1,3-butanediol, 1,8-octanediol, 1,9-nonanediol and 1,10-decanediol.

The diols are preferably soluble in water in that the diols of the general formula (IIa) dissolve in water at 23° C. to an extent of at least 30% by weight, preferably to an extent of at least 40% by weight, more preferably to an extent of at least 50% by weight and most preferably to an extent of at least 60% by weight, examples being 1,3-propanediol and 1,7-heptanediol. Even more preference is given to such postcrosslinkers which are liquid at 25° C.

Preferred postcrosslinkers of the general formula (IIb) are butane-1,2,3-triol, butane-1,2,4-triol, glycerol, trimethylobropane, trimethylolethane, pentaerythritol, ethoxylated glycerol, trimethylolethane or trimethylolpropane each having from 1 to 3 ethylene oxide units per molecule and propoxylated glycerol, trimethylolethane or trimethyloipropane each having from 1 to 3 propylene oxide units per molecule. Preference is further given to 2-tuply ethoxylated or propoxylated neopentylglycol. Particular preference is given to 2-tuply and 3-tuply ethoxylated glycerol, neopentylglycol, 2-ethyl-1,3-propanediol and trimethylolpropane.

Preferred polyhydric alcohols (IIa) and (IIb) have a 23° C. viscosity of less than 3000 mPas, preferably less than 1500 mPas, more preferably less than 1000 mPas, even more preferably less than 500 mPas and at most preferably less than 300 mPas.

Particularly preferred postcrosslinkers of the general formula (III) are ethylene carbonate and propylene carbonate.

A particularly preferred postcrosslinker of the general formula (IV) is 2,2'-bis(2-oxazoline).

The preferred postcrosslinkers minimize side and descendent reactions leading to volatile and hence malodorous compounds. The superabsorbents obtained using the preferred postcrosslinkers are therefore odor neutral in the moistened state also.

A single postcrosslinker from the above selection can be used or any desired mixture of various postcrosslinkers.

The postcrosslinker is generally used in an amount of at least 0.001% by weight, preferably at least 0.02% by weight and more preferably at least 0.05% by weight and also generally at most 2% by weight, preferably at most 1% by weight and more preferably at most 0.3% by weight, for example at most 0.15% by weight or at most 0.095% by weight, all based on the mass of the foundational polymer (the relevant sieve fraction, for example) endowed therewith.

Postcrosslinking is typically carried out by spraying a solution of the postcrosslinker onto the dried foundational polymer particle. After spraying, the postcrosslinker-coated polymer particles are thermally dried, and the postcrosslinking reaction can take place both before and during drying. When surface postcrosslinkers having polymerizable groups are used, surface postcrosslinking can also be effected by free-radically induced polymerization of such groups via commonly used free-radical formers or else via high-energy radiation such as UV light for example. This can take place concurrently with or instead of the use of postcrosslinkers that form covalent or ionic bonds with functional groups on the surface of the foundational polymer particles.

Spraying with the postcrosslinker solution is preferably carried out in mixers having moving mixing implements, such as screw mixers, disk mixers, paddle mixers or shovel mixers, or mixers having other mixing implements. Vertical mixers are particularly preferred, however. But it is also possible for the postcrosslinker solution to be sprayed in a fluidized bed. Suitable mixers are available for example as Pflugschar® plowshare mixers from Gebr. Lödige Maschinenbau GmbH, Elsener-Straße 7-9, 33102 Paderborn, Germany, or as Schugi® Fiexomix® mixers, Vrieco-Nauta® mixers or Turbulizer® mixers from Hosokawa Micron BV, Gildenstraat 26, 7000 AB Doetinchem. Netherlands.

The spray nozzles which can be used are not subject to any limitation. Suitable nozzles and atomization systems are described, for example, in the following references: Zerstäuben von Flüssigkeiten, Expert-Verlag, Vol. 660, Reihe Kontakt & Studium, Thomas Richter (2004) and also in Zerstäubungstechnik, Springer-Verlag, VDI-Reihe, Günter Wozniak (2002). Mono- and polydisperse spraying systems can be used. Among the polydisperse systems, one-material pressurized nozzles (jet- or lamellae-forming), rotational atomizers, two-material atomizers, ultrasound atomizers and impingement nozzles are suitable. In the case of the two-material atomizers, the liquid phase can be mixed with the gas phase either internally or externally. The spray profile of the nozzles is uncritical and may assume any desired form, for example a round jet, flat jet, wide angle round beam or circular ring spray profile. It is advantageous to use a nonoxidizing gas when two-material atomizers are used, particular preference being given to nitrogen, argon or carbon dioxide. The liquid to be sprayed can be supplied to such nozzles under pressure. The liquid to be sprayed can be atomized by decompressing it in the die bore on attainment of a particular minimum velocity. In addition, it is also possible to use one-material nozzles for the purposes of the present invention, for example slot dies or impingement chambers (full-cone nozzles) (for example from Düsen-Schlick GmbH, Germany, or from Spraying Systems Deutschland GmbH, Germany). Such nozzles are also described in EP 0 534 228 A1 and EP 1 191 051 A2.

The postcrosslinkers are typically used in the form of an aqueous solution. When water only is used as the solvent, a surfactant or deagglomeration assistant is advantageously added to the postcrosslinker solution or to the foundational polymer itself. This improves the wetting performance and reduces the tendency to form clumps.

Any anionic, cationic, nonionic and amphoteric surfactants are useful as deagglomeration assistants, preference is given to nonionic and amphoteric surfactants for skin compatibility reasons. The surfactant may also comprise nitrogen. For example, sorbitan monoesters, such as sorbitan monococoate and sorbitan monolaurate, or ethoxylated variants thereof, for example Polysorbat 20®, are added. Suitable deagglomeration assistants further include the ethoxylated and alkoxylated derivatives of 2-propylheptanol which are sold under the Lutensol XL® and Lutensol XP® brands (BASF SE, Carl-Bosch-Straβe 38, 67056 Ludwigshafen, Germany).

The deagalomeration assistant can be metered in separately or added to the postcrosslinker solution. Preferably, the deagglomeration assistant is simply added to the postcrosslinker solution.

The amount of the deagglomeration assistant used, based on foundational polymer, is for example in the range from 0% to 0.1% by weight, preferably in the range from 0% to 0.01% by weight and more preferably in the range from 0% to 0.002% by weight. The deagglomeration assistant is preferably dosed such that the surface tension of an aqueous extract of the swollen foundational polymer and/or of the swollen postcrosslinked superabsorbent at 23° C. is at least 0.060 N/m, preferably at least 0.062 N/m, more preferably at least 0.065 N/m and advantageously at most 0.072 N/m.

The aqueous postcrosslinker solution, in addition to the at least one postcrosslinker, may further comprise a cosolvent. The content of nonaqueous solvent and/or total solvent quantity can be used to adjust the penetration depth of the postcrosslinker into the polymer particles. Industrially highly suitable cosolvents are C1-C6-alcohols, such as methanol, ethanol, n-propanol, isopropanol, n-butanol, sec-butanol, tert-butanol or 2-methyl-1-propanol, C2-C5-diols, such as ethylene glycol, 1,2-propylene glycol or 1,4-butanediol, ketones, such as acetone, or carboxylic esters, such as ethyl acetate. The disadvantage with some of these cosolvents is that they do have characteristic odors.

The cosolvent itself is ideally not a postcrosslinker under the reaction conditions. However, in the limit and depending on residence time and temperature, the cosolvent may end up contributing to crosslinking to some extent. This will be particularly the case when the postcrosslinker is relatively inert and therefore is itself able to form its cosolvent, as with the use for example of cyclic carbonates of the general formula (IV), diols of the general formula (IIIa) or polyols of the general formula (IIIb). Such postcrosslinkers can also be used as a cosolvent when admixed with more reactive postcrosslinkers, since the actual postcrosslinking reaction can then be carried out at lower temperatures and/or shorter residence times than in the absence of the more reactive crosslinker. Since the cosolvent is used in relatively large amounts and will also remain in the product to some extent, it must not be toxic.

The diols of the general formula (IIa), the polyols of the general formula (IIb), and also the cyclic carbonates of the general formula (III) are also useful as cosolvents in the process of the present invention. They perform this function in the presence of a reactive postcrosslinker of the general formula (I) and/or (IV) and/or of a di- or triglycidyl compound. However, preferred cosolvents in the process of the present invention are more particularly the diols of the general formula (IIa), more particularly when the hydroxyl groups are sterically hindered by neighboring groups from participating in a reaction. Such diols are in principle also useful as postcrosslinkers, but for this require distinctly higher reaction temperatures or possibly higher use levels than sterically unhindered diols.

Particularly preferred combinations between a not very reactive postcrosslinker being used as a cosolvent on the one hand and a reactive postcrosslinker on the other are combinations of preferred polyhydric alcohols, diols of the general formula (IIa) and polyols of the general formula (IIb) with amide acetals or carbamates of the general formula (I).

Suitable combinations are for example 2-oxazolidone/1,2-propanediol and N-(2-hydroxyethyl)-2-oxazolidone/1,2-propanediol and also ethylene glycol diglycidyl ether/1,2-propanediol.

Very particularly preferred combinations are 2-oxazolidone/1,3-propanediol and N-(2-hydroxyethyl)-2-oxazolidone/1,3-propanediol.

Further preferred combinations are those with ethylene glycol diglycidyl ether or glycerol diglycidyl or triglycidyl ether with the following solvents, cosolvents or cocrosslinkers: isopropanol, 1,3-propanediol, 1,2-propylene glycol or mixtures thereof.

Further preferred combinations are those with 2-oxazolidone or (2-hydroxyethyl)-2-oxazolidone in the following solvents, cosolvents or cocrosslinkers: isopropanol, 1,3-propanediol, 1,2-propylene glycol, ethylene carbonate, propylene carbonate or mixtures thereof.

The concentration of cosolvent in the aqueous postcrosslinker solution is frequently in the range from 15% to 50% by weight, preferably in the range from 15% to 40% by weight and more preferably in the range from 20% to 35% by weight, based on the postcrosslinker solution. In the case of cosolvents having but limited miscibility with water, it will be advantageous to adjust the aqueous postcrosslinker solution such that there is only one phase, if necessary by lowering the concentration of cosolvent.

There is a preferred embodiment where no cosolvent is used. The postcrosslinker is then only employed as a solution in water with or without an added deagglomeration assistant.

The concentration of the at least one postcrosslinker in the aqueous postcrosslinker solution is typically in the range from 1% to 20% by weight, preferably in the range from 1.5% to 10% by weight and more preferably in the range from 2% to 5% by weight, based on the postcrosslinker solution.

The total amount of postcrosslinker solution based on foundational polymer is typically in the range from 0.3% to 15% by weight and preferably in the range from 2% to 6% by weight.

The actual surface-postcrosslinking by reaction of the surface postcrosslinker with functional groups at the surface of the foundational polymer particles is usually carried out by heating the foundational polymer wetted with surface postcrosslinker solution, which is typically referred to as "drying"

(but must not be confused with the above-described drying of the polymer gel from the polymerization, in which typically very much more liquid has to be removed). The drying can be effected in the mixer itself, by heating the jacket, via heat exchange surfaces or by blowing with warm gases. Simultaneous admixing of the superabsorbent with surface postcrosslinker and drying can take place in a fluidized bed dryer for example. But drying is usually carried out in a downstream dryer, for example a tray dryer, a rotary tube oven, a paddle or disk dryer or a heatable screw. Suitable dryers are available for example as Solidair® or Torusdisc® dryers from Bepex International LLC, 333 N.E. Taft Street. Minneapolis, Minn. 55413, USA, or as paddle or shovel dryers or else as moving bed dryers from Nara Machinery Co., Ltd. Zweigniederlassung Europa, Europaallee 46, 50226 Frechen, Germany.

It is possible to heat the polymer particles via contact surfaces in a downstream dryer, or via a feed of hot warm inert gas, or via a mixture of one or more inert gases with steam, or only with steam alone, for drying and surface postcrosslinking. When the heat is supplied via contact surfaces, it is possible to conduct the reaction under inert gas at slight or complete underpressure. When steam is used to heat the polymer particles directly, it is desirable according to the present invention to operate the dryer at atmospheric pressure or superatmospheric pressure. It can be sensible in this case to split the postcrosslinking step into a heating step with steam and a reaction step under inert gas but without steam. This can be realized in one or more apparatuses. According to the present invention, the polymer particles can be heated up with steam while still in the postcrosslinking mixer. The foundational polymer used can still have a temperature in the range from 10 to 120° C. from preceding operations, and the postcrosslinker solution can have a temperature in the range from 0 to 70° C. More particularly, the postcrosslinker solution can be heated to reduce the viscosity.

Preferred drying temperatures are in the range from 100 to 250° C., preferably in the range from 120 to 220° C., more preferably in the range from 130 to 210° C. and most preferably in the range from 150 to 200° C. The preferred residence time at this temperature in the reaction mixer or dryer is preferably at least 10 minutes, more preferably at least 20 minutes and most preferably at least 30 minutes and typically at most 60 minutes. Typically, the drying is conducted such that the residual moisture content of the superabsorbent is generally at least 0.1% by weight, preferably at least 0.2% by weight and more preferably at least 0.5% by weight, and also generally at most 15% by weight, preferably at most 10% by weight and more preferably at most 8% by weight.

Postcrosslinking can take place under normal atmospheric conditions. By "normal atmospheric conditions" is meant that no technical precautions are taken to reduce the partial pressure of oxidizing gases, such as that of atmospheric oxygen, in the apparatus in which the postcrosslinking reaction predominantly takes place (the "postcrosslinking reactor", typically the dryer). However, it is preferable to conduct the postcrosslinking reaction under reduced partial pressure of oxidizing gases. Oxidizing gases are substances which, at 23° C., have a vapor pressure of at least 1013 mbar and act as oxidizing agents in combustion processes, examples being oxygen, nitrogen oxide and nitrogen dioxide, especially oxygen. The partial pressure of oxidizing gases is preferably less than 140 mbar, more preferably less than 100 mbar, even more preferably less than 50 mbar and most preferably less than 10 mbar. When thermal postcrosslinking is carried out at ambient temperature. i.e. at a total pressure of around 1013 mbar, the total partial pressure of the oxidizing gases is determined via their volume fraction. The fraction of oxidizing gases is preferably less than 14% by volume, more preferably less than 10% by volume, even more preferably less than 5% by volume and most preferably less than 1% by volume.

Postcrosslinking can be carried out under reduced pressure, i.e., at a total pressure of less than 1013 mbar. The total pressure is typically less than 670 mbar, preferably less than 480 mbar, more preferably less than 300 mbar and most preferably less than 200 mbar. When drying and postcrosslinking are carried out under air having an oxygen content of 20.8% by volume, the oxygen partial pressures corresponding to the abovementioned total pressures are 139 mbar (670 mbar), 100 mbar (480 mbar), 62 mbar (300 mbar) and 42 mbar (200 mbar), wherein the respective total pressures are placed between the parentheses. Another way of lowering the partial pressure of oxidizing gases is to introduce nonoxidizing gases, more particularly inert gases, into the apparatus used for postcrosslinking. Suitable inert gases are substances which are present in gaseous form at the postcrosslinking temperature and the given pressure in the postcrosslinking dryer and which, under these conditions, do not have an oxidizing effect on the constituents of the drying polymer particles, examples being nitrogen, carbon dioxide, argon, water vapor, of which nitrogen is preferred. The inert gas rate is generally in the range from 0.0001 to 10 $m^3$, preferably from 0.001 to 5 $m^3$, more preferably from 0.005 to 1 $m^3$ and most preferably from 0.005 to 0.1 $m^3$, based on 1 kg of superabsorbent.

In the process of the present invention, the inert gas not comprising water vapor can be nozzled into the postcrosslinking dryer, but it is particularly preferable to add the inert gas to the polymer particle stream via nozzles in or shortly upstream of the mixer in which the superabsorbent is admixed with surface postcrosslinker.

It will be appreciated that cosolvent vapors removed from the dryer can be recondensed outside the dryer and optionally recycled.

In one embodiment of the process according to the present invention, at least two superabsorbents which were surface-postcrosslinked within the framework of the above description of typical conditions of surface postcrosslinking, yet differently than each other, are subsequently mixed. In a further, preferred embodiment of the process according to the present invention, two or more different sieve cuts of a foundational polymer are separately endowed with surface-postcrosslinking agent, conveniently by spraying in a vertical mixer as described above. This can take place in two or more (depending on the number of sieve fractions used) concurrently operated mixers, or in succession in one mixer, and this naturally requires intermediate storage of sieve cuts endowed with surface-postcrosslinking agent. Surface-postcrosslinking agent type and amount can be the same or different for each sieve fraction.

These sieve cuts can be treated separately from each or one another, each in their own dryer, to perform the surface-postcrosslinking reaction, and mixed thereafter. In a further preferred embodiment, these sieve fractions endowed with surface-postcrosslinking agent, however, are fed into one continuous dryer at various points thereof.

Continuously conveying dryers are dryers in which the product stream to be dried is conveyed continuously from the inlet to the outlet of the dryer. In the process, the contents of the dryer are preferably also agitated in order that the entire contents may come into contact with the heating surfaces. In the process, the dryer contents undergo a certain degree of perhaps even intensive commixing, in that there will usually also be a certain amount of backmixing, but crossmixing dominates by far. In other words, the residence time distribution of the product in the dryer is closer to the residence time distribution of a flow tube reactor than to that of a stirred tank reactor. Typically, the backmixing ratio (i.e., the maximum residence time deviation of 95% by weight of all the particles introduced into the dryer at the first product feed point from the average residence time of all the particles introduced into the dryer at the first product feed point) is not more than 50%, preferably not more than 40% and more preferably not more than 30%. Backmixing ratios of not more than 20% are very particularly preferred. Methods of measuring the backmixing ratio are known, usually the appearance of a marker substance is tracked as a function of time. A customary method of measuring the backmixing ratio in a continuously conveying kneader, that is directly applicable to continuously conveying dryers, is described in WO 2006/034806 A1, for example. A backmixing ratio for product introduced at further feed points can be measured in a similar manner. Backmixing ratio is influenced by the design, more particularly the type and arrangement of the conveying implements, and the operating parameters of the dryer, more particularly the fill level, and can be adjusted to the desired value—all that is known. Dryers suitable for the process of the present invention are particularly disk or paddle dryers or heated screws, preferably paddle dryers.

In a preferred convenient process for producing a mixture which is in accordance with the present invention, already surface postcrosslinker-endowed foundational polymers (which can be but need not be different sieve cuts of the same foundational polymer) are introduced into a continuously conveying dryer at different points thereof. The different feed points into the dryer are spaced apart from each or one another such that the desired effect is achieved. In general, these feed points are at least sufficiently far apart for the difference in the average residence time of the product streams fed in at neighboring feed points, expressed as a percentage, to be greater than the backmixing ratio of the product streams introduced at the two neighboring feed points. A smaller separation is usually not sensible, since the backmixing will in effect not produce any differences in the length of the heat treatment of the individual products added. Preferably, the feed points are spaced apart such that the difference in the average residence time of the product streams added at neighboring feed points, expressed as a percentage, is at least twice the backmixing ratio of the product streams added at the neighboring feed points and more preferably they are spaced apart such that this difference is at least three times as large.

In one simple embodiment, two sieve cuts of a foundational polymer are separately endowed with surface-postcrosslinking agent, one of these sieve cuts is added at the start, i.e., at the first product inlet, of the dryer and the other sieve cut is added halfway between the start and the product outlet of the dryer. Provided the product fill level in the dryer is identical along the length of the dryer (and this can also be arranged differently via the type and arrangement of the conveying implements for example) and also the temperature in the dryer is everywhere the same, this ensures that the second sieve cut added is heat-treated half as intensively as the first.

It will be appreciated that herein it would be similarly possible to classify the foundational polymer after it has been endowed with surface-postcrosslinking agent. However, in purely practical terms, the simplest method for this—sieving—is usually difficult with the typically moist polymer powder following endowment with surface-postcrosslinking agent.

When different sieve cuts of one foundational polymer are used as foundational polymers endowed with surface-postcrosslinking agent, and are endowed in the same way with the same amount of surface-postcrosslinking agent, it is preferable for finer sieve cuts, i.e., sieve cuts having a lower average particle size, to be introduced into the dryer at earlier feed points than coarser sieve cuts. It is similarly preferable for coarser particles to be endowed with less surface-postcrosslinking agent, by weight, and/or with a surface-postcrosslinking agent which, for a given amount, effectuates a lower degree of surface postcrosslinking. The two measures—less or less-crosslinking surface-postcrosslinking agent and less intensive heat treatment—can be used applied individually or combined.

In principle, however, it is also possible to produce a present invention mixture of differingly surface-postcrosslinked superabsorbents by choosing different and hence more particularly differingly reactive surface-postcrosslinking agents and/or differing amount thereof and subsequent conjoint or separate but identical heat treatment, for example conjoint passage through one dryer.

The simplest embodiment of the present invention process for producing a mixture of differingly surface-postcrosslinked superabsorbents is to additionally use an intersieve in the customary sieving off of a foundational polymer, i.e. the removal of over- and undersize, and so to recover the product in the form of two sieve cuts, a comparatively fine sieve cut and a comparatively coarse sieve cut, to endow these two sieve cuts separately with surface-postcrosslinking agent, for example in a vertical mixer in each case, and to introduce them into a continuously conveying dryer at two different points thereof. The further workup then takes place again conjointly in the same way as for a unitarily surface-postcrosslinked superabsorbent.

In one preferred embodiment of the present invention, polyvalent cations are applied to the particle surface before, during or after postcrosslinking in addition to the postcrosslinkers. This is in principle a further surface-postcrosslinking via ionic, noncovalent bonds, but is occasionally also referred to as "complexation" with the metal ions in question, or simply as "coating" with the substances in question (the "complexing agent").

Polyvalent cations are applied by spraying with solutions of divalent or more highly valent cations, usually divalent, trivalent or tetravalent metal cations, but also polyvalent cations such as polymers formally constructed wholly or partly of vinylamine monomers, such as partially or completely hydrolyzed polyvinylamide (so-called "polyvinylamine"), the amine groups of which are always—even at very high pH—partly protonated to ammonium groups. Examples of useful divalent metal cations are in particular the divalent cations of metals of groups 2 (more particularly Mg, Ca, Sr, Ba), 7 (more particularly Mn), 8 (more particularly Fe), 9 (more particularly Co), 10 (more particularly Ni), 11 (more particularly Cu) and 12 (more particularly Zn) of the periodic table of the elements. Examples of useful trivalent metal cations are more particularly the trivalent cations of metals of groups 3 including the lanthanides (more particularly Sc, Y, La, Ce), 8 (more particularly Fe), 11 (more particularly Au), 13 (more particularly Al) and 14 (more particularly Bi) of the periodic table of the elements. Examples of useful tetravalent cations are more particularly the tetravalent cations of metals of the lanthanides (more particularly Ce) and also of group 4 (more particularly Ti, Zr, Hf) of the periodic table of the elements. The metal cations can be used not only alone but also mixed with each or one another. The use of trivalent metal cations is particularly preferred. The use of aluminum cations is very particularly preferred.

Of the metal cations mentioned, any metal salt sufficiently soluble in the solvent to be used is suitable. Metal salts with weakly complexing anions such as, for example, chloride, nitrate and sulfate, hydrogensulfate, carbonate, bicarbonate, nitrate, phosphate, hydrogenphosphate or dihydrogenphosphate are particularly suitable. Preference is given to salts of mono- and dicarboxylic acids, hydroxyacids, ketoacids and also amino acids or basic salts. Examples are, preferably, acetates, propionates, tartrates, maleates, citrates, lactates, malates, succinates. It is similarly preferable to use hydroxides. The use of 2-hydroxycarboxylic acid salts such as citrates and lactates is particularly preferred. Examples of particularly preferred metal salts are alkali and alkaline earth metal aluminates and hydrates thereof, such as sodium aluminate and its hydrates, alkali and alkaline earth metal lactates and citrates and hydrates thereof, aluminum acetate, aluminum propionate, aluminum citrate and aluminum lactate.

The cations and salts mentioned can be used in pure form or in the form of a mixture of various cations or salts. The salts used of the di- and/or trivalent metal cation may comprise further secondary constituents such as still nonneutralized carboxylic acid and/or alkali metal salts of neutralized carboxylic acid. Preferred alkali metal salts are those of sodium, of potassium and of ammonium. They are typically used in the form of an aqueous solution prepared by dissolving the solid salts in water or preferably produced directly as such, which may save drying and purifying steps. It can also be advantageous to use the hydrates of the salts mentioned, because they often are quicker to dissolve in water than the anhydrous salts.

The amount of metal salt used is generally at least 0.001% by weight, preferably at least 0.01% by weight and more preferably at least 0.1% by weight, for example at least 0.4% by weight, and also generally at most 5% by weight, preferably at most 2.5% by weight and more preferably at most 1% by weight, for example at most 0.7% by weight, all based on the mass of the foundational polymer.

The salt of the trivalent metal cation can be used as a solution or suspension. Useful solvents for the metal salts include water, alcohols, DMF, DMSO and also mixtures thereof. Particular preference is given to water and water-alcohol mixtures such as water-methanol, water-1,2-propanediol and water-1,3-propanediol for example.

The treatment of the foundational polymer with solution of a di- or more highly valent cation is carried out in the same way as that with surface postcrosslinker, including the drying step. The surface postcrosslinker and the polyvalent cation can be spray dispensed in a conjoint solution or as separate solutions. The spraying of the metal salt solution onto the superabsorbent particles can take place not only before but also after surface postcrosslinking. In one particularly preferred process, the spraying with the metal salt solution takes place in the same step as the spraying with the crosslinker solution, in which case the two solutions can be spray dispensed separately in succession or concurrently via two nozzles or the crosslinker and metal salt solutions can be spray dispensed conjointly via one nozzle.

Particularly when a tri- or more highly valent metal cation such as aluminum is used for complexation, there is the option of also adding a basic salt of a divalent metal cation or a mixture of such salts. Basic salts are salts capable of raising the pH of an acidic aqueous solution, preferably a 0.1N hydrochloric acid. Basic salts are typically salts of a strong base with a weak acid.

The divalent metal cation of the optional basic salt is preferably a metal cation of group 2 of the periodic table of the elements, more preferably calcium or strontium and most preferably calcium.

The basic salts of the divalent metal cations are preferably salts of weak inorganic acids, weak organic acids and/or salts of amino acids, more preferably hydroxides, bicarbonates, carbonates, acetates, propionates, citrates, gluconates, lactates, tartrates, malates, succinates, maleates and/or fumarates and most preferably hydroxides, bicarbonates, carbonates, propionates and/or lactates. The basic salt is preferably soluble in water. Water-soluble salts are salts which at 20° C. have a water solubility of at least 0.5 g of salt per liter of water, preferably at least 1 g of salt per l of water, more preferably at least 10 g of salt per l of water, even more preferably at least 100 g of salt per l of water and most preferably at least 200 g of salt per l of water. According to the invention, however, it is also possible to use salts that have this minimum solubility at the spraying temperature of the spray solution. It can also be advantageous to use the hydrates of the salts mentioned, because they often are quicker to dissolve in water than the anhydrous salts.

Suitable basic salts of divalent metal cations are for example calcium hydroxide, strontium hydroxide, calcium bicarbonate, strontium bicarbonate, calcium acetate, strontium acetate, calcium propionate, calcium lactate, strontium propionate, strontium lactate, zinc lactate, calcium carbonate and strontium carbonate.

When the solubility in water is insufficient to prepare a sprayable solution of the desired concentration, dispersions of the solid salt in its saturated aqueous solution can also be used. Calcium carbonate, strontium carbonate, calcium sulfite, strontium sulfite, calcium phosphate and strontium phosphate can also be used as aqueous dispersions for example.

The amount of basic salt of the divalent metal cation, based on the mass of the foundational polymer, is typically in the range from 0.001 to 5% by weight, preferably in the range from 0.01 to 2.5% by weight, more preferably in the range from 0.1 to 1.5% by weight, even more preferably in the range from 0.1% to 1% by weight and most preferably in the range from 0.4% to 0.7% by weight.

The basic salt of the divalent metal cation can be used as a solution or suspension. Examples thereof are calcium lactate solutions or calcium hydroxide suspensions. Typically, the salts are sprayed onto the superabsorbent using a water quantity of not more than 15% by weight, preferably not more than 8% by weight, more preferably not more than 5% by weight and most preferably not more than 2% by weight, based on the superabsorbent.

Preferably, an aqueous solution of the basic salt is sprayed onto the superabsorbent. This can be done with the superabsorbent mixture of the present invention but also separately for the individual superabsorbents of the mixture. Conveniently, the basic salt is added concurrently with the surface-postcrosslinking agent, the complexing agent or as a further constituent of the solutions of these agents. For these basic salts, the addition mixed with the complexing agent is preferred. When the solution of the basic salt is not miscible with the solution of the complexing agent without precipitation, the solutions can be sprayed onto the superabsorbent separately in succession or simultaneously from two nozzles.

The superabsorbent mixture or the individual superabsorbents has or have optionally also a reducing compound added to it or them. Examples of reducing compounds are hypophosphites, sulfinates or sulfites. Preference is given to the addition of a sulfinic acid derivative, more particularly a compound of formula (V)

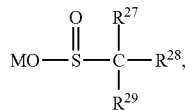
(V)

where
M is a hydrogen atom, an ammonium ion, a monovalent metal ion or one equivalent of a divalent metal ion of groups 1, 2, 8, 9, 10, 12 or 14 of the periodic table of the elements;
$R^{27}$ is OH or $NR^{30}R^{31}$, where $R^{30}$ and $R^{31}$ are each independently H or $C_1$-$C_6$-alkyl;
$R^{28}$ is H or an alkyl, alkenyl, cycloalkyl or aryl group which optionally bears 1, 2 or 3 substituents which are independently selected from the group consisting of $C_1$-$C_6$-alkyl, OH, O—$C_1$-$C_6$-alkyl, halogen and $CF_3$; and
$R^{29}$ is COOM, $SO_3M$, $COR^{30}$, $CONR^{30}R^{31}$ or $COOR^{30}$, where M, $R^{30}$ and $R^{31}$ are each as defined above or else, when $R^{28}$ is aryl which is optionally substituted as indicated above, is H,
salts thereof or mixtures of such compounds and/or salts thereof.

In the above formula, alkyl is straight-chain or branched alkyl of preferably 1-6 and more particularly 1-4 carbon atoms. Examples of alkyl are methyl, ethyl, n-propyl, isopropyl, n-butyl, t-butyl, n-hexyl, etc. The same applies to the alkyl in O-alkyl. Alkenyl is straight-chain or branched alkenyl preferably of 3-8 carbon atoms and more particularly 3-6 carbon atoms. Allyl is a preferred alkenyl. Cycloalkyl is more particularly $C_1$-$C_6$-cycloalkyl, in which case cyclopentyl and cyclohexyl are preferred. Aryl (including in aralkyl) is preferably phenyl or naphthyl. When aryl is a phenyl and is substituted, it preferably has two substituents. These are 2- and/or 4-disposed in particular.

Halogen is F, Cl, Br or I, preferably Cl or Br.

M is preferably an ammonium ion, an alkali metal ion or one equivalent of an alkaline earth metal ion or of a zinc ion. Suitable alkali metal ions are in particular sodium and potassium ions, and suitable alkaline earth metal ions are in particular magnesium, strontium and calcium ions.

$R^{27}$ is preferably hydroxyl or amino.

$R^{28}$ is preferably hydrogen or an alkyl or aryl group which may be substituted as above.

It preferably bears one or two hydroxyl and/or alkoxy substituents.

$R^{29}$ is preferably either COOM or $COOR^{30}$ (M and $R^{30}$ are each as defined above) or else, when $R^{27}$ is aryl which may be substituted as indicated above, a hydrogen atom.

In one preferred embodiment, the superabsorbent mixture or the superabsorbents has or have added to it or them compounds of the above formula (V) where M is an alkali metal ion or one equivalent of an alkaline earth metal or zinc ion; $R^{27}$ is hydroxyl or amino; $R^{28}$ is H or alkyl; and $R^{29}$ is COOM or $COOR^{30}$, where when $R^{29}$ is COOM, M in this COOM radical is H, an alkali metal ion or one equivalent of an alkaline earth metal ion and when $R^{29}$ is $COOR^{30}$, $R^{30}$ is $C_1$-$C_6$-alkyl.

In a further preferred embodiment, the superabsorbent mixture or the superabsorbents has or have added to it or them compounds of the above formula (V) where M is an alkali metal ion or one equivalent of an alkaline earth metal ion or zinc ion; $R^{27}$ is hydroxyl or amino; $R^{28}$ is aryl which is optionally substituted as indicated above, more particularly hydroxyphenyl or $C_1$-$C_4$-alkoxyphenyl; and $R^{29}$ is hydrogen.

The groups 1 (H, Li, Na, K, Rb, Cs, Fr), 2 (Be, Mg, Ca, Sr, Ba, Ra), 8 (Fe, Ru, Os), 9 (Co, Rh, Ir), 10 (Ni, Pd, Pt), 12 (Zn, Cd, Hg) and 14 (C, Si, Ge, Sn, Pb) of the periodic table of the elements in the current numbering by IUPAC (International Union of Pure and Applied Chemistry, 104 T.W. Alexander Drive, Building 19, Research Triangle Park, N.C. 27709, U.S.A., www.iupac.org), the international organization responsible for nomenclature in the field of chemistry, correspond to the groups Ia, IIa, IIb, IVa and VIIIb in the numbering used by CAS (Chemical Abstracts Service, 2540 Olentangy River Road, Columbus, Ohio 43202, U.S.A., www.cas.org).

The sulfinic acid derivatives of the above formula (V) can be added in pure form, but alternatively also in the mixture with the sulfite of the corresponding metal ion and of the corresponding sulfonic acid, which results from the preparation of such compounds in a conventional manner. The preparation of such sulfinic acid derivatives of the above formula is known and described in WO 99/18 067 A1 for example. They are also common commercial products and are available for example in the form of mixtures of the sodium salt of 2-hydroxy-2-sulfinatoacetic acid, the disodium salt of 2-hydroxy-2-sulfonatoacetic acid and sodium bisulfite from L. Brüggemann K G (Salzstrarse 131, 74076 Heilbronn, Germany, www.brueggemann.com) under the designations BRÜGGOLIT® FF6M or BRÜGGOLIT® FF7. alternatively BRUGGOLITE® FF6M or BRUGGOLITE® FF7.

The addition of one or more reducing compounds to the superabsorbent mixture or superabsorbents is effected in a conventional manner by adding the compounds in substance, as a solution or as a suspension in a solvent or suspension medium during or after the production of the superabsorbent mixture or superabsorbents. Typically, a solution or suspension of the reducing compound in water or an organic solvent is used, for example in an alcohol or polyol or in mixtures thereof. Examples of suitable solvents or suspension media are water, isopropanol/water, 1,3-propanediol/water and propylene glycol/water, wherein the mixing mass ratio is preferably in the range from 20:80 to 40:60. The solution or suspension may have a surfactant added to it. When reducing compounds are added, they are generally added in an amount of at least 0.0001% by weight, preferably at least 0.001% by weight and more preferably at least 0.025% by weight, for example at least 0.1% by weight or at least 0.3% by weight, and also generally at most 3% by weight, preferably at most 2.5% by weight and more preferably at most 1.5% by weight, for example at most 1% by weight or 0.7% by weight, all based on the total weight of the superabsorbent.

The reducing compound is generally mixed with the superabsorbent mixture or superabsorbents in exactly the same way as the surface postcrosslinker solution or suspension applied to the superabsorbent for surface postcrosslinking. The reducing compound can be applied to a foundational polymer as a constituent part of the surface postcrosslinker solution or of one of its components, i.e., added to the solution of the surface postcrosslinker or one of its components. The superabsorbent coated with surface-postcrosslinking agent and reducing compound then passes through the further process steps necessary for surface postcrosslinking, for example a thermally induced reaction of the surface-postcrosslinking agent with the superabsorbent as per the process of the present invention. This process is comparatively simple and economical.

When very high stability to discoloration in prolonged storage is essential, the reducing compound is applied in a separate process step, preferably after surface postcrosslinking. When the reducing compound is applied in the form of a solution or suspension, it is applied to the already surface-postcrosslinked superabsorbent or the mixture of the present invention in the same way as the surface-postcrosslinking agent is applied to the foundational polymer. Usually, but not necessarily, this is followed—just as in surface postcrosslinking—by heating to dry the superabsorbent again. However, the temperature setting for this drying is generally at most 110° C., preferably at most 100° C. and more preferably at most 90° C. in order that undesired reactions of the reducing compound may be avoided. The temperature setting chosen is such that, in view of the residence time in the drying assembly, the desired water content is achieved for the superabsorbent or superabsorbent mixture. It is also perfectly possible—and convenient—to add the reducing compound individually or together with other customary auxiliaries, for example dustproofing agents, anti-caking agents or water to remoisten the superabsorbent, as described hereinbelow for these auxiliaries, for example in a cooler disposed downstream of the surface-postcrosslinking stage. The temperature of the polymer particles in this case is between 0° C. and 190° C., preferably less than 160° C., more preferably less than 130° C. even more preferably less than 100° C. and most preferably less than 70° C. The polymer particles, if appropriate after coating, are speedily cooled down to temperatures below the decomposition temperature of the reducing compound.

When surface postcrosslinking and/or treatment with complexing agent is followed by a drying step, it is advantageous—but not absolutely necessary—to cool the product after drying. Cooling can be done continuously or batchwise, conveniently the product is for this purpose continuously conveyed into a cooler disposed downstream of the dryer. Any apparatus known for removing heat from pulverulent solids can be used for this purpose, more particularly any apparatus mentioned above as drying apparatus, provided it is operated not with a heating medium but with a cooling medium such as cooling water for example, so that the walls and also, depending on the design, the stirrer implements or other heat-exchange surfaces do not carry heat into the superabsorbent or superabsorbent mixture but remove it therefrom. Preference is given to the use of coolers in which the product is agitated, i.e., cooled mixers, for example shovel coolers, disk coolers or paddle coolers. The superabsorbent can also be cooled in a fluidized layer by blowing with a cooled gas such as cold air. Cooling conditions are adjusted so as to obtain a superabsorbent having the temperature desired for further processing. Typically, the average residence time in the cooler is generally at least 1 minute, preferably at least 3 minutes and more preferably at least 5 minutes and also generally at most 6 hours, preferably at most 2 hours and more preferably at most 1 hour, and cooling performance is such that the product obtained has a temperature of generally at least 0° C., preferably at least 10° C. and more preferably at least 20° C. and also generally at most 100° C., preferably at most 80° C. and more preferably at most 60° C.

The surface-postcrosslinked superabsorbent or the mixture is optionally ground and/or sieved in a conventional manner. Grinding is typically not necessary here, but it is usually advisable for product agglomerates or fines to be sieved off to achieve the desired particle size distribution for the product. Agglomerates and fines are either discarded or preferably returned at a suitable point into the process in a conventional manner, agglomerates after comminution. The particle sizes desired for surface-postcrosslinked superabsorbents are the same as in the case of foundational polymers.

Optionally, the superabsorbent particles may additionally, if desired, be surface coated at every stage of their manufacturing process with any known coating, such as film-forming polymers, thermoplastic polymers, dendrimers, polycationic polymers (such as polyvinylamine, polyethyleneimine or polyallylamine for example), water-insoluble polyvalent metal salts, for example magnesium carbonate, magnesium oxide, magnesium hydroxide, calcium carbonate, calcium sulfate or calcium phosphate, any water-soluble mono- or polyvalent metal salt known to a person skilled in the art, for example aluminum sulfate, salts of sodium, of potassium, of zirconium or of iron, or hydrophilic inorganic particles, such as clay minerals, fumed silica, colloidal silica sols such as Levasil® for example, titanium dioxide, aluminum oxide and magnesium oxide. Examples of useful alkali metal salts are sodium sulfate, potassium sulfate, sodium lactate, potassium lactate, sodium citrate, potassium citrate, sodium sorbate and potassium sorbate. Additional benefits can be achieved as a result, examples being reduced caking tendency of the end or intermediate product at every stage of the manufacturing process, improved processing properties or a further enhanced ability to transmit liquid (SFC). When the additives are used in the form of dispersions and applied by spraying, they are preferably used as aqueous dispersions and it is preferable to additionally apply a dedusting agent to fix the additive on the surface of the superabsorbent. The dedusting agent is then added either directly to the dispersion of the inorganic pulverulent additive or else it can be added as a separate solution before, during or after the application of the inorganic pulverulent additive, by spraying. The most preferable version is to simultaneously apply postcrosslinker, deduster and pulverulent inorganic additive by spraying in the postcrosslinking stage. In a further preferred version of the process, however, the dedusting agent is added separately in the cooler, for example by spraying from above, from below or from the side. Particularly suitable dedusting agents which can also serve to fix pulverulent inorganic additives to the surface of the superabsorbent particles are polyethylene glycols having a molecular weight in the range from 400 to 20 000 g/mol, polyglycerol, 3- to 100-tuply ethoxylated polyols, such as trimethylolpropane, glycerol, sorbitol and neopentylglycol. Of particular suitability are 7- to 20-tuply ethoxylated glycerol or trimethylolpropane, for example Polyol TP 70® (Perstorp, SE). The latter have the particular advantage that they lower the surface tension of an aqueous extract of the superabsorbent particles only insignificantly.

It is similarly possible to adjust the superabsorbents of the present invention to a desired water content by adding water.

Optionally, the superabsorbents of the present invention are endowed with further addition agents that stabilize against discoloration. Examples are more particularly known stabilizers against discoloration, more particularly reducing substances. Preference among these is given to solid or dissolved salts of phosphinic acid ($H_3PO_2$) as well as phosphonic acid ($H_3PO_2$) itself. All phosphinates of alkali metals, including ammonium, and of alkaline earth metals are suitable for example. Particular preference is given to aqueous solutions of phosphinic acid that comprise phosphinate ions and also at least one cation selected from sodium, potassium, ammonium calcium, strontium, aluminum, magnesium.

Preference is similarly given to salts of phosphonic acid ($H_3PO_3$) as well as phosphonic acid ($H_3PO_3$) itself. All primary and secondary phosphonates of alkali metals, including ammonium, and of alkaline earth metals are suitable for example. Particular preference is given to aqueous solutions of phosphonic acid that comprise primary and/or secondary phosphinate ions and also at least one cation selected from sodium, potassium, calcium, strontium.

All coatings, solids, addition agents and auxiliary substances can each be added in separate process steps, but usually the most convenient method of adding them—if they are not added during the admixing of the foundational polymer with surface-postcrosslinking agent—is to add them to the superabsorbent in the cooler, for example by spraying a solution or adding in finely divided solid or in liquid form.

The superabsorbent mixture of the present invention generally has a Centrifuge Retention Capacity (CRC) of at least 5 g/g, preferably at least 10 g/g and more preferably at least 20 g/g. Further suitable minimum CRC values are for example 25 g/g, 30 g/g or 35 g/g. CRC is typically not above 40 g/g. A typical CRC range for surface-postcrosslinked superabsorbents is from 28 to 33 g/g.

The superabsorbent mixture of the present invention typically has an Absorbency Under Load (AUL 0.7 psi, method of measurement see hereinbelow) of at least 18 g/g, preferably at least 20 g/g, more preferably at least 22 g/g, even more preferably at least 23 g/g and most preferably at least 24 g/g, and typically not above 30 g/g.

The superabsorbent mixture of the present invention further has a Saline Flow Conductivity (SFC, method of measurement see hereinbelow) of at least $10 \times 10^{-7}$ cm$^3$ s/g, preferably at least $30 \times 10^{-7}$ cm$^3$ s/g, more preferably at least $50 \times 10^{-7}$ cm$^3$ s/g, even more preferably at least $80 \times 10^{-7}$ cm$^3$ s/g and most preferably at least $100 \times 10^{-7}$ cm$^3$ s/g, and usually not above $1000 \times 10^{-7}$ cm$^3$ s/g.

The present invention further provides hygiene articles comprising superabsorbent mixtures of the present invention, preferably ultrathin diapers comprising an absorbent layer consisting of 50% to 100% by weight, preferably 60% to 100% by weight, preferably 70% to 100% by weight, more preferably 80% to 100% by weight and most preferably 90% to 100% by weight of the superabsorbent mixture of the present invention, not counting the envelope surrounding the absorbent layer, of course.

The superabsorbent mixtures of the present invention are also very particularly advantageous in the manufacture of laminates and composite structures as described in US 2003/0181115 and also US 2004/0019342 for example. In addition to the hot-melt adhesives described in the two references for producing such novel absorbent structures and, more particularly, the hot-melt adhesive fibers described in US 2003/0181115, to which the superabsorbent particles are attached, the superabsorbent mixtures of the present invention are also useful in the manufacture of completely analogous structures using UV-crosslinkable hot-melt adhesives marketed as AC-Resin® (BASF SE, Carl-Bosch-Straße 38, 67056 Ludwigshafen, Germany) for example. These UV-crosslinkable hot-melt adhesives have the advantage of being processable at as low a temperature as 120 to 140° C., and hence they are more compatible with many thermoplastic substrates. A further significant advantage is that UV-crosslinkable hot-melt adhesives are generally recognized as very safe by toxicologists and also do not give rise to outgassings in the hygiene articles. A very significant advantage in connection with the superabsorbent mixtures of the present invention is the property of UV-crosslinkable hot-melt adhesives of not tending to yellow during processing and crosslinking. This is advantageous particularly when ultrathin or partly transparent hygiene articles are to be produced. The combination of superabsorbent mixtures of the present invention with UV-crosslinkable hot-melt adhesives is therefore particularly advantageous. Suitable UV-crosslinkable hot-melt adhesives are described for example in EP 0 377 199 A2, EP 0 445 641 A1, U.S. Pat. No. 5,026,806, EP 0 655 465 A1 and EP 0 377 191 A2 for example.

The superabsorbent mixture of the present invention can also be used in other technical fields where liquids, more particularly water or aqueous solutions are absorbed. These fields are for example storage, packaging, transportation (as constituents of packaging material for water- or moisture-sensitive articles, for example for flower transportation, also as protection against mechanical impacts); animal hygiene (in cat litter); food packaging (transportation of fish, fresh meat; absorption of water, blood in fresh fish or meat packs); medicine (wound plasters, water-absorbing material for burn dressings or other weeping wounds), cosmetics (carrier material for pharmachemicals and medicaments, rheumatic plasters, ultrasonic gel, cool gel, cosmetic thickeners, sun protection); thickeners for oil-in-water and water-in-oil emulsions; textiles (moisture regulation in textiles, shoe inserts, for evaporative cooling, for example in protective clothing, gloves, headbands); chemical engineering applications (as a catalyst for organic reactions, to immobilize large functional molecules such as enzymes, as adhesion agent in relation to agglomerations, heat storage media, filter aids, hydrophilic component in polymeric laminates, dispersants, superplasticizers); as auxiliaries in powder injection molding, in building construction and engineering (installation, in loam-based renders, as a vibration-inhibiting medium, auxiliaries in tunnel excavations in water-rich ground, cable sheathing); water treatment, waste treatment, water removal (deicing agents, reusable sand bags); cleaning; agritech (irrigation, retention of melt water and dew deposits, composting additive, protection of forests against fungal/insect infestation, delayed release of active components to plants); for firefighting or for fire protection; coextrusion agents in thermoplastic polymers (for example to hydrophilicize multilayered films); production of self-supporting film sheet and of thermoplastic moldings able to absorb water (e.g., rain and dew water storage films for agriculture; superabsorbent-containing films for keeping fruit and vegetables fresh which are packed in moist films; superabsorbent-polystyrene coextrudates, for example for food packaging such as meat, fish, poultry, fruit and vegetables); or as a carrier substance in formulations of active components (pharma, crop protection).

The present invention articles for absorbing fluid differ from existing ones in comprising the superabsorbent mixture of the present invention.

The present invention also provides a process for producing articles for absorbing fluid, more particularly hygiene articles, which comprises producing the article in question by utilizing the superabsorbent mixture of the present invention. In other respects, processes for producing such articles using superabsorbent are known.

Test Methods

The superabsorbent is tested using the test methods described hereinbelow.

The hereinbelow described "WSP" standard test methods are described in: "Standard Test Methods for the Nonwovens Industry", 2005 edition, jointly issued by the "Worldwide Strategic Partners" EDANA (European Disposables and Nonwovens Association, Avenue Eugene Plasky, 157, 1030 Brussels, Belgium, www.edana.org) and INDA (Association of the Nonwoven Fabrics Industry, 1100 Crescent Green, Suite 115, Cary, N.C. 27518, U.S.A., www.inda.org). This publication is available both from EDANA and INDA.

Measurements described hereinbelow should all be carried out, unless otherwise stated, at an ambient temperature of 23±2° C. and a relative humidity of 50±10%. The superabsorbent particles are efficiently commixed before measurement, unless otherwise stated.

Centrifuge Retention Capacity (CRC)

The centrifuge retention capacity of the superabsorbent is determined as per the standard test method No. WSP 241.5-02 "Centrifuge retention capacity".

Absorbency Under Load of 0.7 psi (AUL0.7 psi)

The absorbency under a pressure of 4826 Pa (0.7 psi) of the superabsorbent is determined similarly to the standard test method No. WSP 242.2-05 "Absorption under pressure", except that a weight of 49 g/cm² (leading to a pressure of 0.7 psi) is used instead of a weight of 21 g/cm² (leading to a pressure of 0.3 psi).

Saline Flow Conductivity SFC)

The flow conductivity of a swollen layer of gel formed by the superabsorbent by absorption of a liquid is determined under a confining pressure of 0.3 psi (2068 Pa) as described in EP 640 330 A1 as the Gel Layer Permeability (GLP) of a swollen gel layer of superabsorbent particles (referred to there as "AGM" for "absorbent gelling material"), although the apparatus described in the aforementioned patent application at page 19 and FIG. 8 is modified to the effect that the glass frit 40 is no longer used, the piston 39 is made of the same plastics material as the cylinder 37 and now comprises 21 equally sized holes uniformly distributed over the entire contact surface. The procedure and evaluation of the measurement remains unchanged from EP 640 330 A1. Flow rate is recorded automatically.

Saline flow conductivity (SFC) is computed as follows:

$$\text{SFC } [cm^3 s/g] = (Fg(t=0) \times L0)/(d \times A \times WP),$$

where $Fg(t=0)$ is the flow rate of NaCl solution in g/s obtained from a linear regression analysis of the $Fg(t)$ data of the flow rate determinations by extrapolation to $t=0$; $L0$ is the thickness of the gel layer in cm; d is the density of the NaCl solution in g/cm³; A is the area of the gel layer in cm²; and WP is the hydrostatic pressure on the gel layer in dyn/cm².

Moisture content of superabsorbent (residual moisture content, water content)

The water content of the superabsorbent particles is determined as per the standard test method No. WSP 230.2-05 "Moisture content".

Average Particle Size

The average particle size of the product fraction is determined as per the standard test method No. WSP 220.2-05 "Particle size distribution".

EXAMPLES

Example 1

Preparing a Foundational Polymer (Comparative)

A Pflugschar® plowshare mixer of the VT 5R-MK type, having a 5 liter capacity equipped with a heating/cooling jacket (manufacturer: Gebr. Lödige Maschinenbau GmbH; Elsener-Straße 7-9, 33102 Paderborn, Germany) was initially charged with a reaction mixture formed of 183 g of water, 239 g of acrylic acid and 2148 g of a 37.3% by weight sodium acrylate solution (100 mol % neutralized) and also 2.8 g of 3-tuply ethoxylated glycerol triacrylate and inertized for 20 minutes by bubbling nitrogen therethrough. In the process, the reaction mixture was temperature controlled such that the subsequent addition of initiator took place at about 20° C. Under agitation, 2.39 g of sodium persulfate (dissolved in 13.53 g of water), 0.05 g of ascorbic acid (dissolved in 10.18 g of water) and 0.14 g of 30% by weight hydrogen peroxide (dissolved in 1.28 g of water) were rapidly added to the mixer as initiators in succession. The reaction ensued speedily. From attainment of an internal temperature of 30° C. the jacket of the mixer was heated with hot heat transfer medium at 80° C. After the maximum temperature was reached, cooling fluid (−12° C.) was used to cool the resulting gel in the mixer down to below 50° C. and the gel was then discharged. The gel was spread onto two wire-bottomed trays and dried at 160° C. in a circulating air drying cabinet for 2 hours. The dried gel was subsequently comminuted using a laboratory ultracentrifugal mill (manufacturer: Retsch GmbH; Rheinische Straße 36, 42781 Haan, Germany; Type ZM 200). The product was sieved to recover four product fractions having particle sizes from 150 to 300 μm, from 300 to 400 μm, from 400 to 500 μm and from 500 to 710 μm.

The AUL 0.7 psi and CRC values of these sieve cuts of a foundational polymer were:

| fraction [μm] | AUL 0.7 psi [g/g] | CRC [g/g] |
|---|---|---|
| 150-300 | 7.1 | 34.1 |
| 300-400 | 7.5 | 34.7 |
| 400-500 | 7.7 | 35.5 |
| 500-710 | 7.9 | 35.0 |

Example 2

Surface-Postcrosslinking the Model Foundational Polymer (Comparative)

Equal portions of the four sieve cuts from example 1 were combined to form a model foundational polymer comprising 25% by weight each of every sieve cut.

1.2 kg of foundational polymer obtained according to the procedure of example 1 were sprayed with crosslinker solution in a Pflugschar® plowshare mixer of type VT 5R-MK having a 5 liter capacity and equipped with heating/cooling jacket (manufacturer: Gebr. Lödige Maschinenbau GmbH; Elsener-Straße 7-9, 33102 Paderborn, Germany) at room temperature under intensive commixing. A customary two-material spray nozzle as also used for laboratory spray dryers was used (manufacturer: Büchi Labortechnik GmbH, Am Porscheplatz 5, 45127 Essen, Germany). The composition of the crosslinker solution, based on the foundational polymer used, was: 0.10% by weiaht of N-(2-hydroxyethyl)oxazolidinone, 1.10% by weiaht of n-propanol and also 2.80% by weight of water. The moist polymer was then dried in a second Pflugschar® plowshare mixer of the same design at a polymer temperature of 185° C. for 60 minutes with a 5 g polymer sample being taken every 10 minutes.

The time course of the development of AUL 0.7 psi, CRC and SFC during the heat treatment is shown in the table which follows:

| time [min] | AUL 0.7 psi [g/g] | CRC [g/g] | SFC [$10^{-7}$ cm³ s/g] |
|---|---|---|---|
| 0 | — | 34.7 | — |
| 10 | — | 36.0 | — |
| 20 | — | 35.5 | — |
| 30 | 19.5 | 31.9 | 5 |
| 40 | 24.3 | 29.9 | 27 |

-continued

| time [min] | AUL 0.7 psi [g/g] | CRC [g/g] | SFC [$10^{-7}$ cm$^3$ s/g] |
|---|---|---|---|
| 50 | 24.5 | 27.7 | 43 |
| 60 | 24.3 | 26.6 | 65 |

Example 3

Comparative

Following conclusion of the experimental series of example 2 (i.e., after 60 minutes), the polymer was removed and again separated by sieving into the individual sieve cuts.

The AUL 0.7 psi, CRC and SFC values of these sieve cuts were:

| fraction [μm] | AUL 0.7 psi [g/g] | CRC [g/g] | SFC [$10^{-7}$ cm$^3$ s/g] |
|---|---|---|---|
| 150-300 | 23.6 | 25.0 | 70 |
| 300-400 | 23.9 | 26.7 | 72 |
| 400-500 | 24.6 | 28.5 | 82 |
| 500-710 | 24.3 | 28.3 | 68 |

Comparison with the corresponding values of the mixture (last line of the table of example 2) shows that AUL and CRC of the conjointly surface-postcrosslinked mixture correspond essentially to the mean of the corresponding values of the sieve cuts, but that the mixture SFC is determined by the SFC of the sieve cut having the lowest SFC.

Example 4

A 150-300 μm sieve cut obtained according to example 1 was surface postcrosslinked as described in example 2 for the mixture. The time course of the development of AUL 0.7 psi, CRC and SFC during the heat treatment is shown in the table which follows:

| time [min] | AUL 0.7 psi [g/g] | CRC [g/g] | SFC [$10^{-7}$ cm$^3$ s/g] |
|---|---|---|---|
| 0 | 7.1 | 34.1 | — |
| 10 | — | 35.5 | — |
| 20 | — | 34.5 | — |
| 30 | 17.7 | 31.5 | 0 |
| 40 | 21.7 | 29.1 | 8 |
| 50 | 24.3 | 27.7 | 20 |
| 60 | 24.8 | 27.0 | 34 |

Example 5

A 300-400 μm sieve cut obtained according to example 1 was surface postcrosslinked as described in example 2 for the mixture. The time course of the development of AUL 0.7 psi, CRC and SFC during the heat treatment is shown in the table which follows:

| time [min] | AUL 0.7 psi [g/g] | CRC [g/g] | SFC [$10^{-7}$ cm$^3$ s/g] |
|---|---|---|---|
| 0 | 7.5 | 34.7 | — |
| 10 | — | 35.6 | — |
| 20 | — | 34.5 | — |
| 30 | 20.7 | 31.4 | 3 |
| 40 | 24.8 | 29.0 | 18 |
| 50 | 25.0 | 28.0 | 36 |
| 60 | 24.5 | 26.9 | 52 |

Example 6

A 400-500 μm sieve cut obtained according to example 1 was surface postcrosslinked as described in example 2 for the mixture. The time course of the development of AUL 0.7 psi, CRC and SFC during the heat treatment is shown in the table which follows:

| time [min] | AUL 0.7 psi [g/g] | CRC [g/g] | SFC [$10^{-7}$ cm$^3$ s/g] |
|---|---|---|---|
| 0 | 7.7 | 35.5 | — |
| 10 | — | 36.9 | — |
| 20 | — | 35.4 | — |
| 30 | 24.4 | 32.3 | 29 |
| 40 | 25.6 | 30.0 | 95 |
| 50 | 25.7 | 28.7 | 122 |
| 60 | 24.9 | 27.6 | 137 |

Example 7

A 500-710 μm sieve cut obtained according to example 1 was surface postcrosslinked as described in example 2 for the mixture. The time course of the development of AUL 0.7 psi, CRC and SFC during the heat treatment is shown in the table which follows:

| time [min] | AUL 0.7 psi [g/g] | CRC [g/g] | SFC [$10^{-7}$ cm$^3$ s/g] |
|---|---|---|---|
| 0 | 7.9 | 35.0 | — |
| 10 | — | 35.4 | — |
| 20 | — | 35.4 | — |
| 30 | 25.1 | 32.5 | 36 |
| 40 | 26.2 | 31.2 | 90 |
| 50 | 25.8 | 29.1 | 136 |
| 60 | 25.2 | 28.1 | 169 |

The comparison of examples 4 to 7 shows that the relatively fine sieve cuts, when subjected to the identical endowment with surface-postcrosslinking agent, need an appreciably more intensive heat treatment than the coarser ones to establish permeability. Accordingly, appropriately adapted surface postcrosslinking of comparatively fine particles makes it possible to achieve a higher permeability for the mixture as a whole.

Example 8

The model foundational polymer obtained according to example 1 was postcrosslinked as described in example 2 except that the heat treatment was carried out for 50 minutes. Similarly, a sample of each sieve cut of the foundational polymer was similarly surface-postcrosslinked and subjected to the heat treatment for the duration reported in the table which follows. The four surface-postcrosslinked sieve cuts were subsequently recombined to form a mixture. The CRC, AUL 0.7 psi and SFC values achieved are likewise reported in the table which follows.

| sample (postcrosslinked) | duration of heat treatment [min] | AUL 0.7 psi [g/g] | CRC [g/g] | SFC [$10^{-7}$ cm$^3$ s/g] |
|---|---|---|---|---|
| model foundational polymer | 50 | 24.6 | 27.9 | 48 |
| 150-300 μm | 70 | 24.4 | 25.6 | 50 |
| 300-400 μm | 55 | 25.6 | 28.5 | 56 |
| 400-500 μm | 35 | 25.2 | 31.3 | 60 |
| 500-710 μm | 32 | 26.2 | 32.1 | 53 |
| mixture of sieve cuts | 48 (averaged) | 25.6 | 29.0 | 48 |

In these tests, surface postcrosslinking was carried out such that the mixture of separately postcrosslinked sieve cuts is subjected to virtually the same averaged heat-treatment duration, and the same permeability is achieved, compared with the conjointly surface-postcrosslinked mixture. There was no optimization for high permeability. The procedure corresponds to separate endowment of four sieve cuts of a foundational polymer with identical amounts of the same surface-postcrosslinking agent and their introduction into a continuously conveying dryer at four separate points which correspond to the particular heat-treatment time reported as an average residence time for the particular sieve cut in the dryer. These tests show that the process of the present invention thereby, for the same permeability, provides a higher absorbency for the mixture of separately postcrosslinked sieve cuts.

We claim:

1. A process for producing a mixture of superabsorbents having differing surface postcrosslinking by mixing differingly surface-postcrosslinked superabsorbents, wherein different sieve fractions of a base polymer are separately admixed with a surface-postcrosslinking agent, subsequently surface-postcrosslinked by differing heat-treatment duration, and mixed, wherein the heat treatment utilizes a continuously conveying and heated dryer and the different base polymer sieve fractions endowed with surface postcrosslinking agent are fed in at various points of the dryer.

2. A process for producing a mixture of superabsorbents having differing surface postcrosslinking by mixing differingly surface-postcrosslinked superabsorbents, wherein an aqueous solution of a monomer mixture comprising:
   a) at least one ethylenically unsaturated acid-functional monomer which optionally is at least partly present as a salt,
   b) at least one crosslinker,
   c) at least one initiator,
   d) optionally one or more ethylenically unsaturated monomer copolymerizable with the monomer mentioned under a),
   e) optionally one or more water-soluble polymer, is polymerized, the polymer obtained is dried, comminuted, classified into at least two sieve cuts, wherein the at least two sieve cuts are differingly surface-postcrosslinked with a surface-postcrosslinking agent, mixed, and then fed in at various points of a continuously conveying and heated dryer for a subsequent heat treatment.

3. A process for producing articles for absorbing fluid, which comprises incorporating a superabsorbent mixture prepared by the process of claim 1 in the article.

* * * * *